(12) United States Patent
Marczyk et al.

(10) Patent No.: US 11,446,026 B2
(45) Date of Patent: Sep. 20, 2022

(54) SURGICAL STAPLES AND END EFFECTORS FOR DEPLOYING THE SAME

(71) Applicant: Covidien LP, Mansfield, MA (US)

(72) Inventors: Stanislaw Z. Marczyk, Stratford, CT (US); Simon R. Grover, Cambridge (GB)

(73) Assignee: Covidien LP, Mansfield, MA (US)

( * ) Notice: Subject to any disclaimer, the term of this patent is extended or adjusted under 35 U.S.C. 154(b) by 226 days.

(21) Appl. No.: 16/803,071

(22) Filed: Feb. 27, 2020

(65) Prior Publication Data

US 2020/0187938 A1 Jun. 18, 2020

Related U.S. Application Data

(62) Division of application No. 15/834,485, filed on Dec. 7, 2017, now Pat. No. 10,603,034, which is a division
(Continued)

(51) Int. Cl.
 *A61B 17/072* (2006.01)
 *A61B 17/068* (2006.01)
 *A61B 17/064* (2006.01)

(52) U.S. Cl.
 CPC ........ *A61B 17/068* (2013.01); *A61B 17/0644* (2013.01); *A61B 17/072* (2013.01);
(Continued)

(58) Field of Classification Search
 CPC ................ A61B 17/068; A61B 17/072; A61B 17/07207; A61B 17/115; A61B 17/1155;
A61B 2017/07214; A61B 2017/07228; A61B 2017/07242; A61B 2017/07271; A61B 2017/07257; A61B 2017/07285
(Continued)

(56) References Cited

U.S. PATENT DOCUMENTS

| 3,079,606 A | 3/1963 | Bobrov et al. |
| 3,490,675 A | 1/1970 | Green et al. |

(Continued)

FOREIGN PATENT DOCUMENTS

| AU | 198654765 | 9/1986 |
| CA | 2773414 A1 | 11/2012 |

(Continued)

OTHER PUBLICATIONS

Australian Examination Report dated Jul. 24, 2018, corresponding to Australian Application No. 2014259547; 3 pages.
(Continued)

*Primary Examiner* — Scott A Smith

(57) ABSTRACT

An end effector includes an anvil and a cartridge assembly having a plurality of surgical staples disposed in a cavity defined therein. The cartridge assembly may include a movable driver or sled configured to deploy the surgical staple from the cavity into tissue. The surgical staple may include a linear leg and an arcuate leg extending therefrom. The linear leg may include a protruding portion to provide pressure to tissue captured by the surgical staple. A three-dimensional and/or self-supporting surgical staple may interlock its two legs upon deployment thereof.

20 Claims, 12 Drawing Sheets

Related U.S. Application Data of application No. 14/513,629, filed on Oct. 14, 2014, now Pat. No. 9,867,613.

(60) Provisional application No. 61/918,018, filed on Dec. 19, 2013.

(52) U.S. Cl.
CPC .. *A61B 17/07207* (2013.01); *A61B 17/07292* (2013.01); *A61B 2017/07214* (2013.01); *A61B 2017/07228* (2013.01); *A61B 2017/07271* (2013.01); *A61B 2017/07278* (2013.01)

(58) Field of Classification Search
USPC .............. 227/19, 175.1, 176.1, 175.2, 180.1; 606/1, 75, 139, 151, 219
See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,305,539 A * | 12/1981 | Korolkov ............. A61B 17/072 227/135 |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |

(56) References Cited

U.S. PATENT DOCUMENTS

| | | |
|---|---|---|
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,571,285 A | 11/1996 | Chow et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,394 A | 10/1999 | Robertson |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |

(56) References Cited

U.S. PATENT DOCUMENTS

| | | |
|---|---|---|
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |

(56) References Cited

U.S. PATENT DOCUMENTS

| | | | |
|---|---|---|---|
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |

(56) References Cited

U.S. PATENT DOCUMENTS

| | | |
|---|---|---|
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,225,980 B1 | 7/2012 | Rivera |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |

(56) References Cited

U.S. PATENT DOCUMENTS

| | | |
|---|---|---|
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,261,958 B1 | 9/2012 | Knodel |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |

(56) References Cited

U.S. PATENT DOCUMENTS

| | | | |
|---|---|---|---|
| 8,512,402 B2 | 8/2013 | Marczyk et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,529,600 B2 | 9/2013 | Woodard, Jr. et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,870,049 B2 | 10/2014 | Amid |
| 9,016,541 B2 | 4/2015 | Viola et al. |
| 9,655,615 B2 * | 5/2017 | Knodel ............... A61B 17/068 |
| 9,867,613 B2 | 1/2018 | Marczyk et al. |
| 9,872,683 B2 | 1/2018 | Hopkins |
| 10,603,034 B2 | 3/2020 | Marczyk et al. |
| 11,051,812 B2 * | 7/2021 | Hopkins .......... A61B 17/07207 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0010241 A1 | 1/2005 | Milliman et al. |
| 2005/0103819 A1 | 5/2005 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0078803 A1 | 4/2008 | Shelton et al. |
| 2008/0078807 A1 * | 4/2008 | Hess .................... A61B 17/072 227/181.1 |
| 2008/0082126 A1 * | 4/2008 | Murray ............ A61B 17/07207 606/221 |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |

(56) References Cited

U.S. PATENT DOCUMENTS

| | | |
|---|---|---|
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277948 A1 | 11/2009 | Beardsley et al. |
| 2009/0277949 A1 | 11/2009 | Viola et al. |
| 2009/0283568 A1 | 11/2009 | Racenet et al. |
| 2009/0308907 A1 | 12/2009 | Nalagatla et al. |
| 2010/0006620 A1 | 1/2010 | Sorrentino et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2010/0305552 A1 | 12/2010 | Shelton, IV et al. |
| 2011/0006099 A1 | 1/2011 | Hall et al. |
| 2011/0006101 A1 | 1/2011 | Hall et al. |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0068148 A1 | 3/2011 | Hall et al. |
| 2011/0087276 A1 | 4/2011 | Bedi et al. |
| 2011/0101069 A1 | 5/2011 | Bombard et al. |
| 2011/0108601 A1 | 5/2011 | Clark |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132964 A1 | 6/2011 | Weisenburgh, II et al. |
| 2011/0139851 A1 | 6/2011 | McCuen |
| 2011/0147433 A1 | 6/2011 | Shelton, IV et al. |
| 2011/0155781 A1 | 6/2011 | Swensgard et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295270 A1 | 12/2011 | Giordano et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0061446 A1 | 3/2012 | Knodel et al. |
| 2012/0061450 A1 | 3/2012 | Kostrzewski |
| 2012/0074196 A1 | 3/2012 | Shelton, IV et al. |
| 2012/0074200 A1 | 3/2012 | Schmid et al. |
| 2012/0080333 A1 | 4/2012 | Woodard, Jr. |
| 2012/0080474 A1 | 4/2012 | Farascioni |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080498 A1 | 4/2012 | Shelton, IV et al. |
| 2012/0080499 A1 | 4/2012 | Schall et al. |
| 2012/0080502 A1 | 4/2012 | Morgan et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0223123 A1 | 9/2012 | Baxter, III et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0255986 A1 | 10/2012 | Petty et al. |
| 2012/0286021 A1 | 11/2012 | Kostrzewski |
| 2012/0286022 A1 | 11/2012 | Olson et al. |
| 2012/0292369 A1 | 11/2012 | Munro, III et al. |
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325893 A1 | 12/2012 | Pastorelli et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |

(56) References Cited

U.S. PATENT DOCUMENTS

| | | |
|---|---|---|
| 2013/0068818 A1 | 3/2013 | Kasvikis |
| 2013/0068821 A1 | 3/2013 | Huitema et al. |
| 2013/0075443 A1 | 3/2013 | Giordano et al. |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | Racenet et al. |
| 2013/0112730 A1 | 5/2013 | Whitman et al. |
| 2013/0112732 A1 | 5/2013 | Aranyi et al. |
| 2013/0112733 A1 | 5/2013 | Aranyi et al. |
| 2013/0119109 A1 | 5/2013 | Farascioni et al. |
| 2013/0126581 A1 | 5/2013 | Yates et al. |
| 2013/0126582 A1 | 5/2013 | Shelton, IV et al. |
| 2013/0126586 A1 | 5/2013 | Zhang et al. |
| 2013/0140343 A1 | 6/2013 | Knodel |
| 2013/0144333 A1 | 6/2013 | Viola |
| 2013/0233908 A1* | 9/2013 | Knodel ............ A61B 17/068 227/177.1 |
| 2014/0263570 A1* | 9/2014 | Hopkins .......... A61B 17/07207 227/176.1 |

FOREIGN PATENT DOCUMENTS

| | | |
|---|---|---|
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 2090253 A2 | 8/2009 |
| EP | 2090254 A1 | 8/2009 |
| EP | 2583630 A2 | 4/2013 |
| EP | 2586382 A2 | 5/2013 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 6/1975 |
| JP | 2001087272 | 4/2001 |
| SU | 128848 A1 | 11/1959 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 97/28745 A1 | 8/1997 |
| WO | 2004032760 A2 | 4/2004 |
| WO | 2009071070 A2 | 6/2009 |
| WO | 2013122808 A1 | 8/2013 |
| WO | 2013151820 A1 | 10/2013 |

OTHER PUBLICATIONS

European Extended Search Report dated Jun. 10, 2015, corresponding to European Application No. 14199033.3; 5 pages.

* cited by examiner

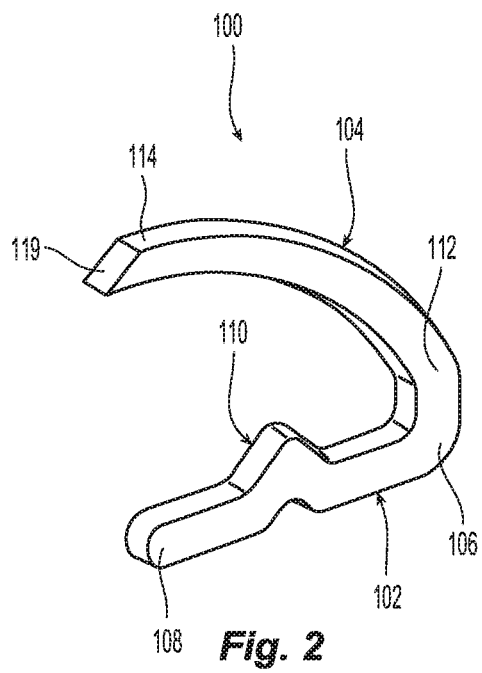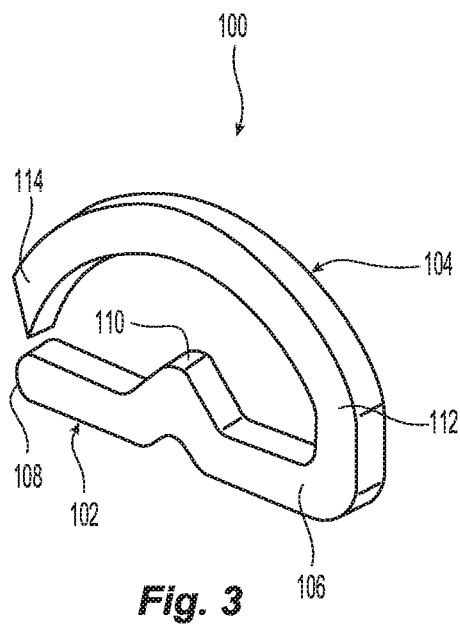
Fig. 2      Fig. 3
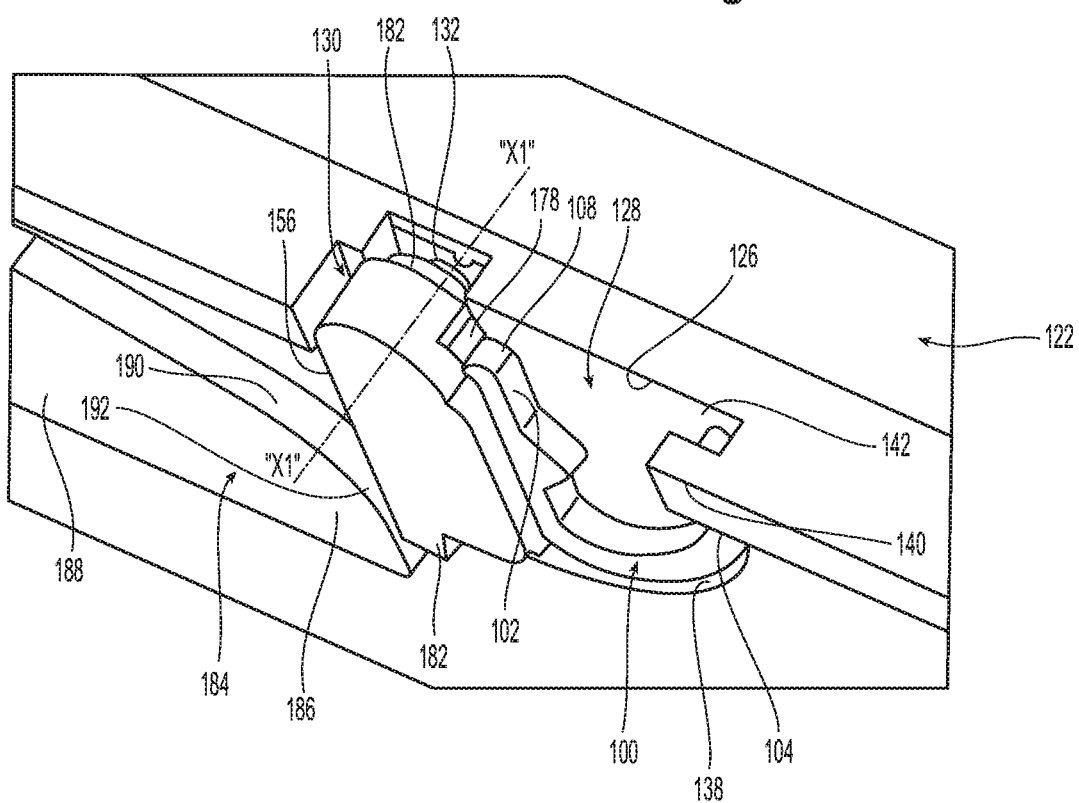
Fig. 4

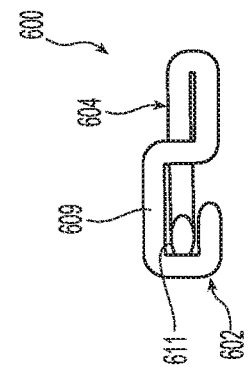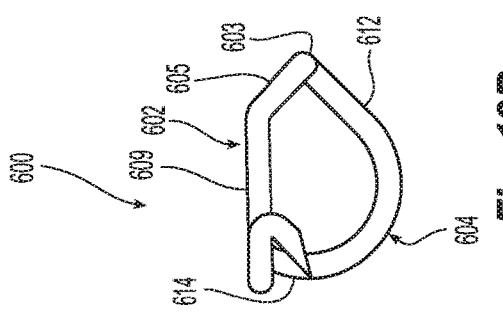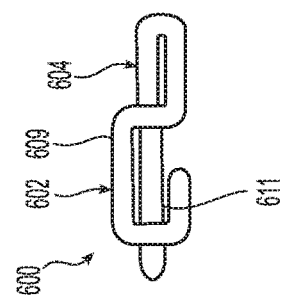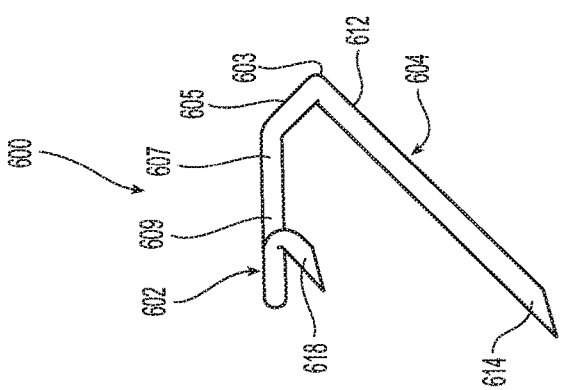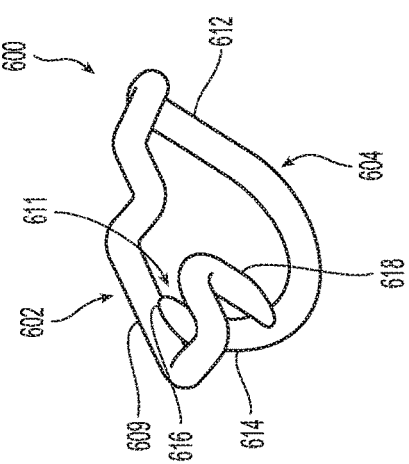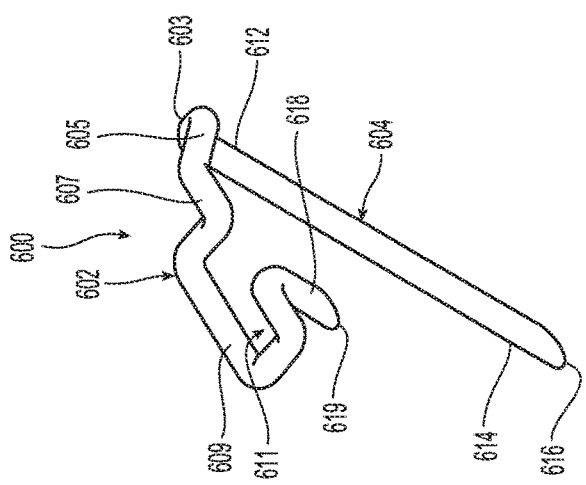

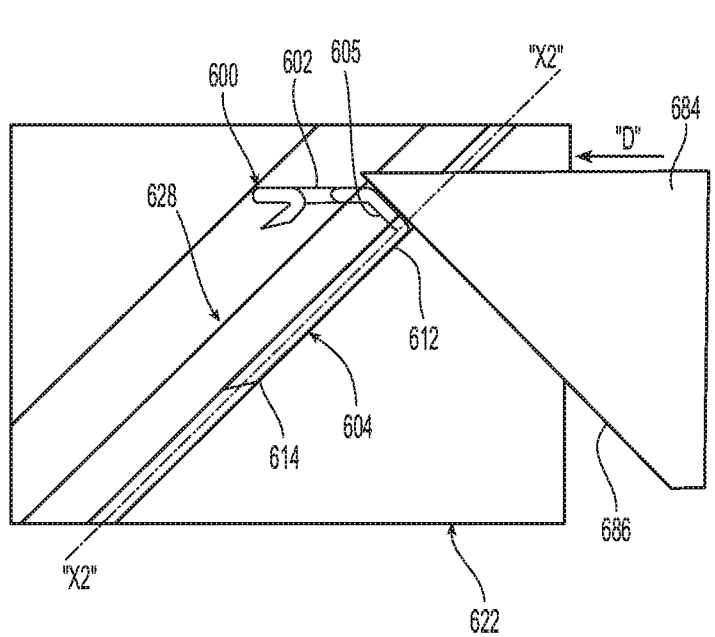
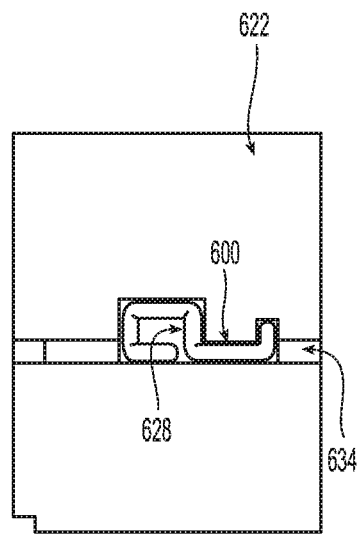
Fig. 22  Fig. 23
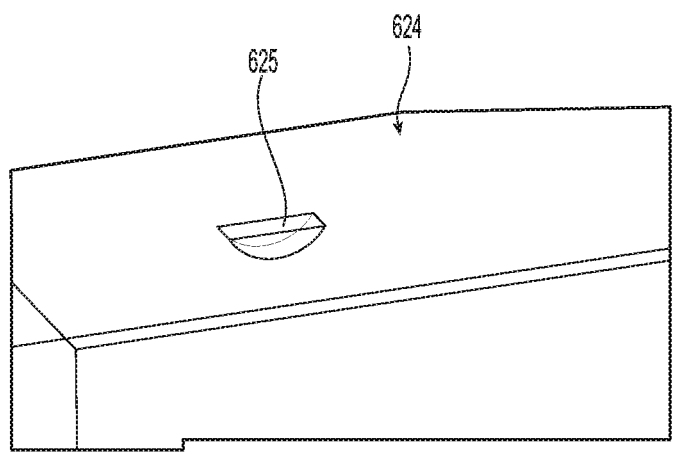
Fig. 24

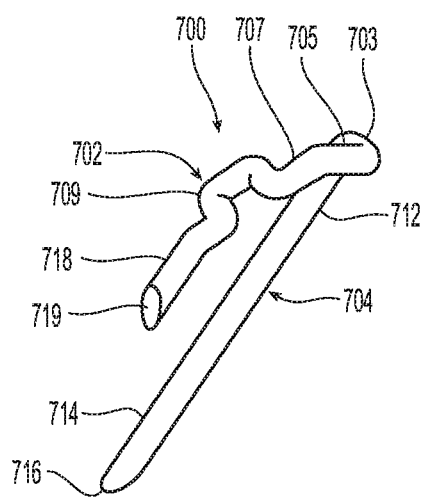
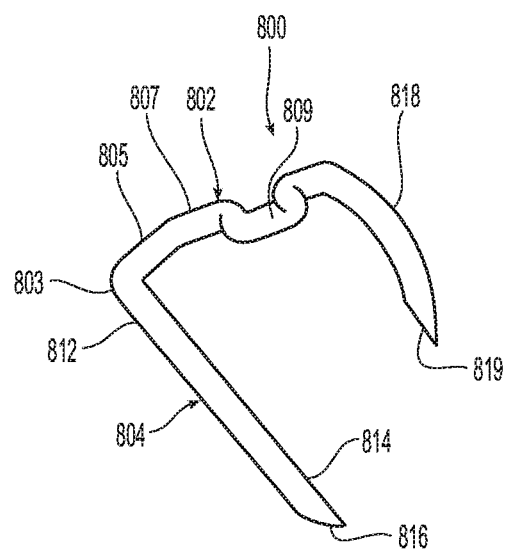
*Fig. 25A*      *Fig. 26A*
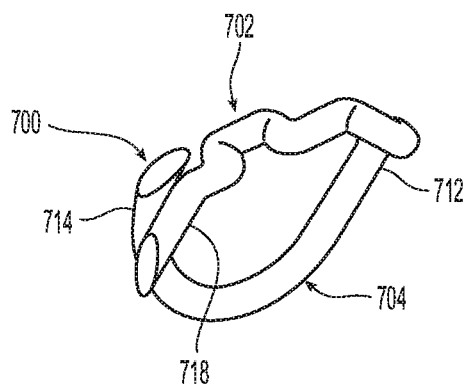
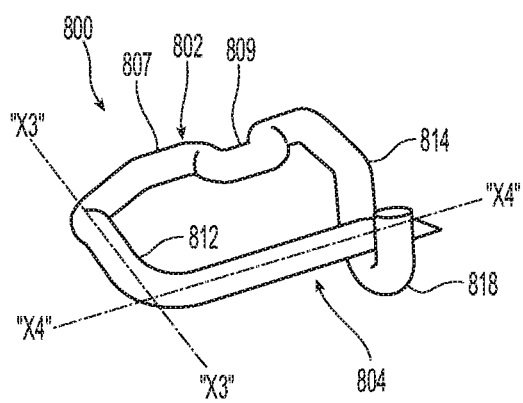
*Fig. 25B*      *Fig. 26B*
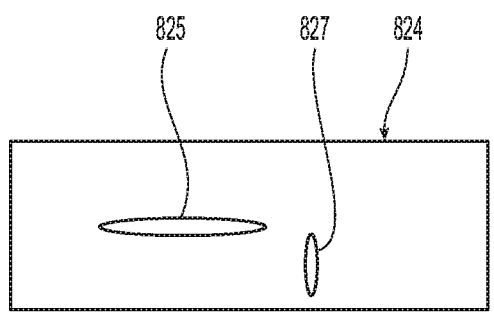
*Fig. 27*

SURGICAL STAPLES AND END EFFECTORS FOR DEPLOYING THE SAME

CROSS-REFERENCE TO RELATED APPLICATION(S)

The present application is a divisional of U.S. patent application Ser. No. 15/834,485, filed on Dec. 7, 2017, now U.S. Pat. No. 10,603,034, which is a divisional of U.S. patent application Ser. No. 14/513,629, filed Oct. 14, 2014, now U.S. Pat. No. 9,867,613, which claims the benefit of and priority to U.S. Provisional Application No. 61/918,018 filed on Dec. 19, 2013, the entire contents of each of which are incorporated by reference herein.

BACKGROUND

1. Technical Field

The present disclosure relates to formable surgical fasteners and, more particularly, to surgical staples for use in surgical staplers having an end effector including a cartridge assembly for deploying the surgical staples and an anvil for forming the surgical staples. The present disclosure also relates to cartridge assemblies configured to carry and deploy the surgical staples and anvil assemblies for forming the surgical staples.

2. Background of Related Art

Many varieties of surgical fastening apparatus are known in the art, some of which are specifically adapted for use in various surgical procedures including, but not limited to, end-to-end anastomosis, open gastrointestinal anastomosis, endoscopic gastrointestinal anastomosis, and transverse anastomosis. Suitable examples of apparatus which may be used during the course of these procedures can be seen in U.S. Pat. Nos. 5,915,616; 6,202,914; 5,865,361; and 5,964,394, each of which is hereby incorporated by reference herein in its entirety.

In general, a surgical fastening apparatus will include an anvil that is approximated relative to a fastener cartridge during use. The anvil includes depressions that are aligned with, and/or are in registration with slots defined in the cartridge, through which the fasteners will emerge, to effectuate formation. The fastener cartridge typically has one or more rows of fasteners disposed laterally or radially of a longitudinal slot that is configured to accommodate a knife, or other such cutting element, such that tissue can be simultaneously cut and joined together. Depending upon the particular surgical fastening apparatus, the rows of fasteners may be arranged in a linear or non-linear, e.g. circular, semi-circular, or otherwise arcuate configuration.

Various types of surgical fasteners are well known in the art, including but not limited to unitary fasteners and two-part fasteners. Unitary fasteners generally include a pair of legs adapted to penetrate tissue and are connected by a backspan from which they extend. The staples are formed into a closed configuration, such as a "B" shaped configuration. Typically, the two-part fastener includes legs that are barbed and connected by a backspan. The legs are engaged and locked into a separate retainer piece that is usually located in the anvil. In use, the two-part fastener is pressed into the tissue so that the barbs penetrate the tissue and emerge from the other side where they are then locked into the retainer piece. The retainer piece prevents the two-part fastener from dislodging from the tissue. The two-part fasteners are not intended to be unlocked or removable. The fasteners are generally made of a bioabsorbable material.

During each of the aforementioned surgical procedures, the tissue is initially gripped or clamped between the anvil and cartridge such that individual fasteners can be ejected from the cartridge, through the slots, and forced through the clamped tissue. Thereafter, the fasteners are formed by driving them into the depressions formed in the anvil.

Laparoscopic Endo GIA™ reloads or cartridge assemblies are usually 12 mm in diameter. Some cartridge assemblies used to staple relatively thick tissue are 15 mm in diameter. "B" staples use linear pushers to keep the staples constrained within a pocket of a cartridge assembly during their deployment. "B" staples are guided from all sides to ensure acceptable forming. Traditional staple-pusher-sled configurations, however, are too big to fit a 5 mm diameter stapler.

Accordingly, there is a growing need to make staplers having cartridge assemblies that are smaller than 12 mm in diameter, with 5 mm cartridge assemblies being the most desirable. There is also a growing need for surgical staples that occupy less space within a cartridge assembly prior to deployment. Pediatric, thoracic and hepato-biliary and pancreatic surgeons could benefit from such devices. Further, it would simplify port management if a cartridge assembly could fit into a 12 mm port. Smaller cartridge assemblies will also enable new multi-firing staplers, which may be capable of being reloaded inside of body cavities.

It would therefore be desirable to provide a staple configuration for a staple designed to penetrate tissue and contact an anvil pocket on the opposing side of tissue, which, in cooperation with conventional cartridge and anvil technology, minimizes staple size and therefore cartridge assembly size.

SUMMARY

In accordance with one aspect of the present disclosure, a surgical staple is provided for use in a surgical stapler. The surgical stapler has an end effector with opposing jaws. An anvil is located on one jaw and a cartridge is located on an opposing jaw. The jaws are movable between spaced apart and approximated positions. The anvil has anvil pockets against which the staples are formed as at least one leg of each staple is urged into contact with the anvil. The surgical staple may include a linear leg and an arcuate leg extending therefrom. The linear leg may include a protruding portion to provide pressure to tissue captured by the surgical staple.

In accordance with another aspect of the present disclosure, a self-supporting surgical staple is provided. The self-supporting surgical staple can be directly driven and formed without the need for any additional supporting components. The self-supporting surgical staple is dimensioned such that it can be constrained within a pocket or cavity of a cartridge assembly while permitting only one degree of freedom, along which the surgical staple will be formed. The self-supporting surgical staple may include a first, linear leg extending at an angle relative to a second leg. The self-supporting surgical staple may further include a connector extending at an angle relative to the first and second legs configured for abutting engagement with a driver, sled, or wedge of a cartridge assembly.

Surgical staples of the present disclosure allow for the use of smaller diameter laparoscopic staplers. The surgical staples can be made from titanium or stainless steel and can be fabricated from sheet metal or wire. In some embodiments, a bump in the surgical staples helps to hold the surgical staples securely in a pocket of a cartridge assembly. It is contemplated that a backspan of the surgical staples can have a short spike to stabilize the surgical staples against tissue. In some embodiments, the surgical staples can include a bump to achieve even tissue compression. In embodiments, the surgical staples may be partially coined to achieve a desired stiffness and decrease the size of an entry wound during insertion into tissue.

In accordance with another aspect of the present disclosure, an end effector of a surgical stapler is provided. The end effector includes a cartridge assembly and an anvil. The cartridge assembly may have a plurality of surgical staples disposed in a cavity defined therein. The cartridge assembly may include a movable pusher bar and/or sled configured to deploy the surgical staple from the cavity into tissue. The pusher bar at least partially secures a surgical staple in the cavity of the cartridge assembly. Upon engagement of the sled with the pusher bar, the pusher bar rotates within the cavity about an axis to deploy the surgical staple from the cavity into engagement with the anvil and tissue.

In some aspects of the present disclosure, a cartridge assembly includes a locking shelf to prevent a pusher bar from being ejected from the cartridge assembly.

In other embodiments, the cartridge assembly does not include a pusher bar such that the sled directly engages a surgical staple to deploy the surgical staple from the cavity into engagement with the anvil and tissue.

In another embodiment of the present disclosure, an anvil is provided that includes two anvil pockets disposed in perpendicular relation to one another.

BRIEF DESCRIPTION OF THE DRAWINGS

Various embodiments are described herein with reference to the drawings, wherein:

FIG. 2 is a perspective view of a surgical staple in an unformed configuration in accordance with an embodiment of the present disclosure;

FIG. 3 is a perspective view of the surgical staple shown in FIG. 2 in a formed configuration;

FIG. 4 is a perspective, cutaway view of a cartridge assembly, in accordance with an embodiment of the present disclosure, with the surgical staple shown in FIG. 2 disposed therein;

FIG. 18A is a perspective view of a surgical staple in an unformed configuration in accordance with another embodiment of the present disclosure;

FIG. 18B is a perspective view of the surgical staple shown in FIG. 18A in a formed configuration;

FIG. 19A is a side view of the surgical staple shown in FIG. 18A in the unformed configuration;

FIG. 19B is a side view of the surgical staple shown in FIG. 18A in the formed configuration;

FIG. 20A is a top view of the surgical staple shown in FIG. 18A in the unformed configuration;

FIG. 20B is a top view of the surgical staple shown in FIG. 18A in the formed configuration;

FIG. 22 is a side view of the cartridge assembly shown in FIG. 21 and a driver deploying the surgical staple shown in FIG. 18A;

FIG. 23 is a top view of the cartridge assembly and surgical staple shown in FIG. 22;

FIG. 24 is a perspective view of the anvil assembly shown in FIG. 21;

FIG. 25A is a perspective view of a surgical staple in an unformed configuration in accordance with another embodiment of the present disclosure;

FIG. 25B is a perspective view of the surgical staple shown in FIG. 25A in a formed configuration;

FIG. 26A is a perspective view of a surgical staple in an unformed configuration in accordance with another embodiment of the present disclosure;

FIG. 26B is a perspective view of the surgical staple shown in FIG. 26A in a formed configuration; and FIG. 27 is a top view of an anvil having two anvil pockets in accordance with an embodiment of the present disclosure.

DETAILED DESCRIPTION OF THE EMBODIMENTS

Figure 1:
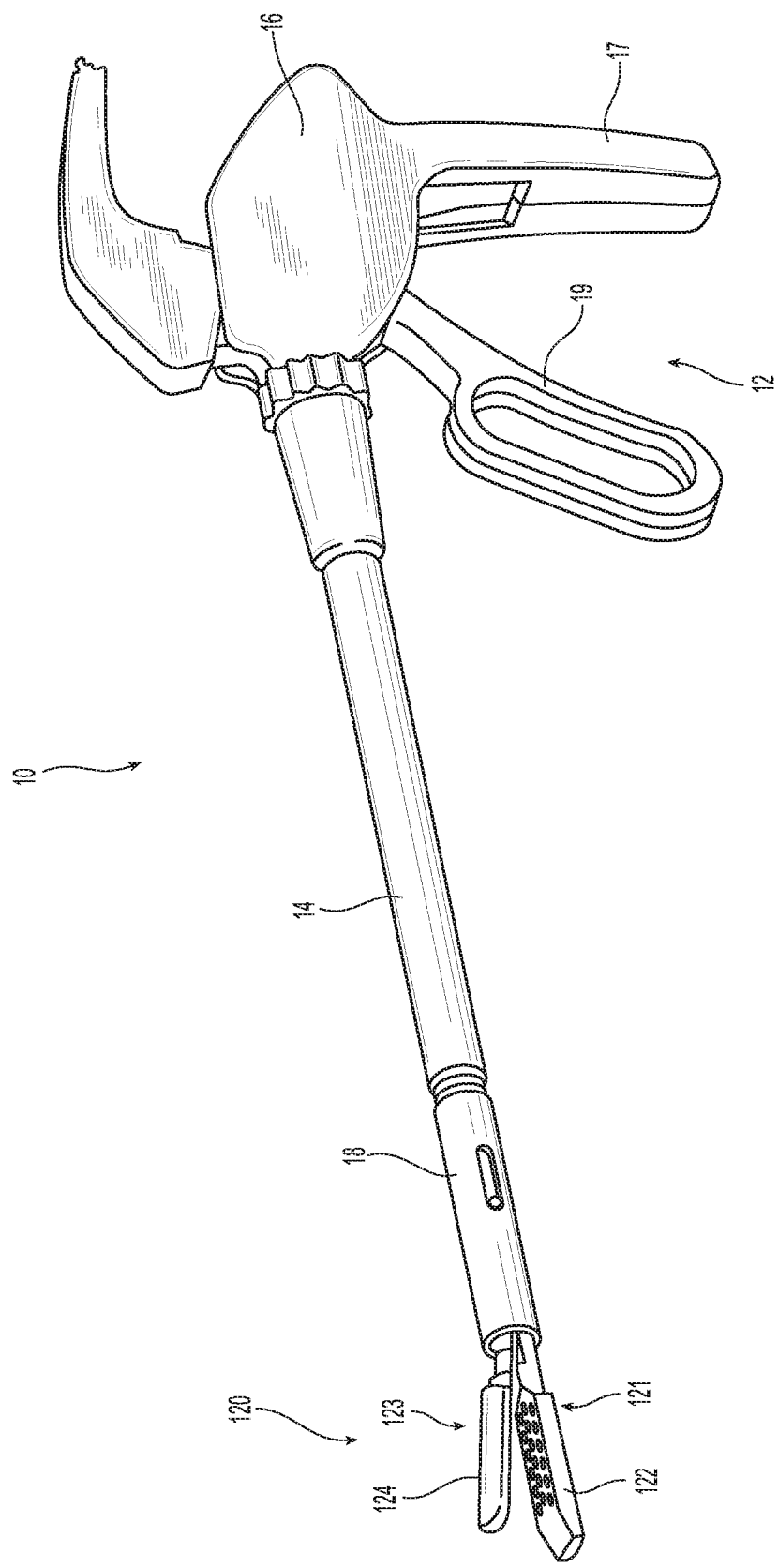
FIG. 1 is a perspective view of a surgical stapler in accordance with an embodiment of the present disclosure.
Figure 5:
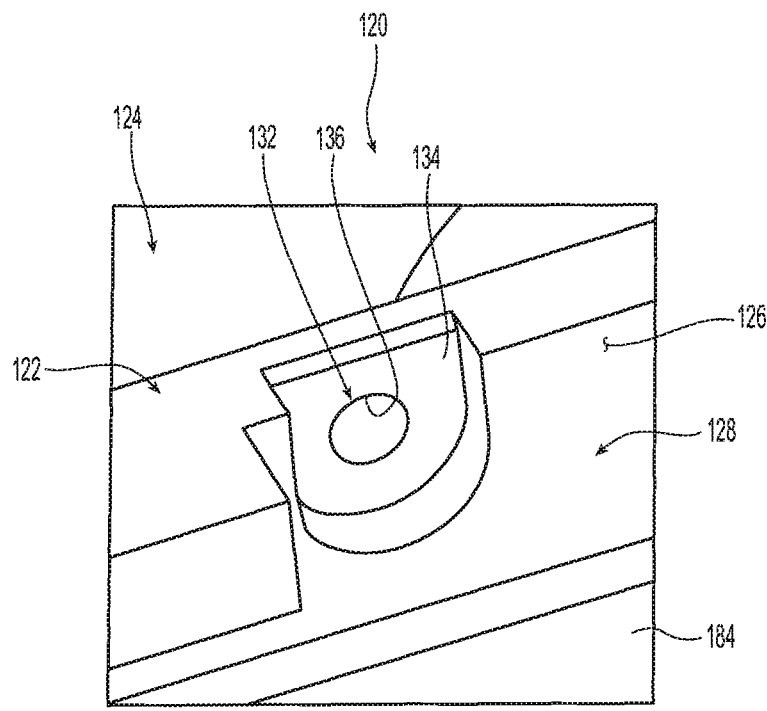
FIG. 5 is a cutaway view of a cavity defined in the cartridge assembly shown in FIG. 4.
Figure 6:
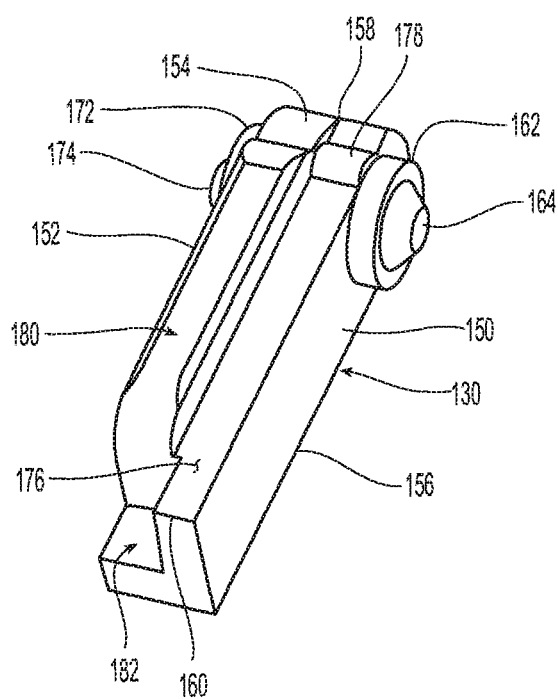
FIG. 6 is a perspective view of a pusher bar of the cartridge assembly shown in FIG. 4.
Figure 7:
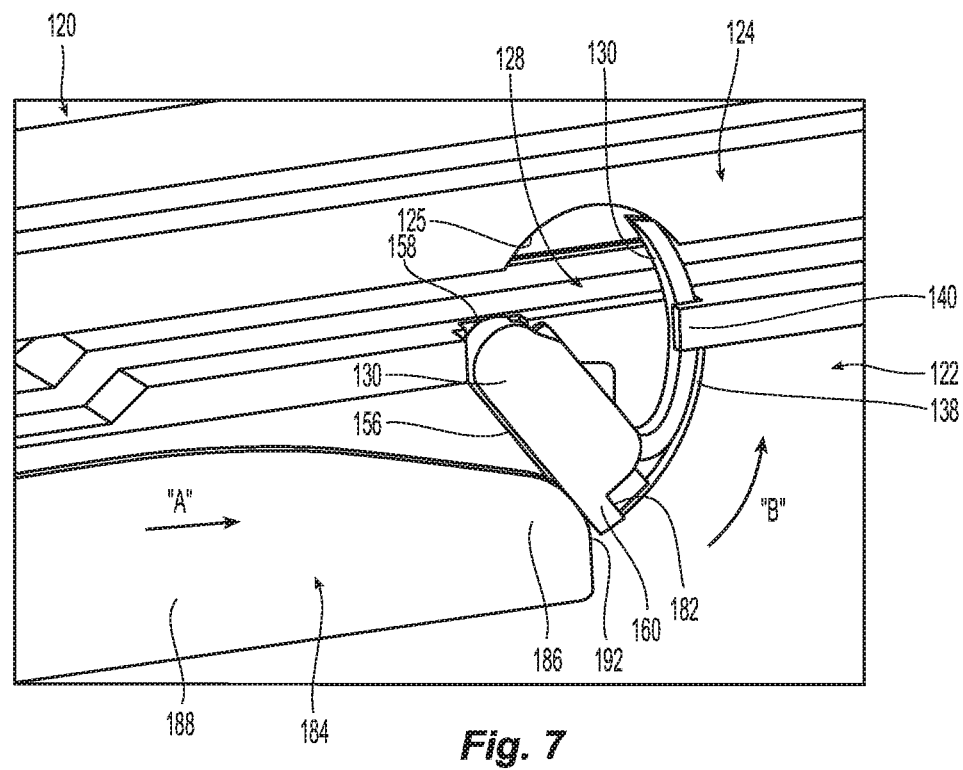
FIG. 7 is a perspective, cutaway view of an end effector including an anvil and the cartridge assembly shown in FIG. 4 deploying the surgical staple shown in FIG. 2.

Embodiments of the presently disclosed surgical staples and end effectors will now be described in detail with reference to the drawings, in which like reference numerals designate identical or corresponding elements in each of the several views.

With reference to FIG. 1, a surgical fastener applying apparatus 10 according to an embodiment of the present disclosure will be discussed. Surgical fastener applying apparatus 10 is used to sequentially apply a plurality of surgical fasteners to tissue, and may be of the re-usable or disposable variety. Surgical fastener applying apparatus 10 includes a handle 12, an elongated shaft 14 extending distally therefrom, and an end effector 120 coupled to a distal end 18 of the elongated shaft 14. Actuation of the handle 12 advances a drive rod distally to operate the end effector 120. However, other handles may be used, such as, for example, motor-driven, hydraulic, ratcheting, etc. In general, end effector 120 is adapted to clamp, sequentially fasten together, and sever adjacent tissue segments along a cut-line. Accordingly, end effector 120 includes a pair of opposed jaws 121, 123 pivotally coupled with respect to one another and respectively including a surgical fastener cartridge assembly 122 and an anvil 124.

In operation, surgical fastener applying apparatus 10 is fired similarly to and in accordance with other known surgical stapling instruments. For a detailed discussion of the approximation and firing of surgical stapling instrument 10, reference is made to commonly assigned U.S. Pat. No. 5,865,361, the entire contents of which have already been incorporated herein by reference. The handle 12 includes a housing 16, which includes stationary handle member 17. A movable trigger 19 is pivotably supported within the housing 16 and is biased away from the stationary handle member 17. Movement of the movable trigger 19 in the direction of the stationary handle member 17 imparts a driving force to an actuation shaft within the housing 16 causing it to advance linearly in a distal direction. The staple cartridge assembly 122 and anvil 124 are moved closer relative to each other and a force is transmitted to the ejectors or pushers positioned adjacent to surgical fasteners disposed within slots of the staple cartridge assembly 122 thereby ejecting the surgical fasteners and driving the surgical fasteners against a staple forming surface of the anvil 124.

Referring specifically to FIGS. 2 and 3, a new surgical staple 100 is provided, which is configured for disposal in a cartridge assembly, such as, for example, cartridge assembly 122 described with reference to FIG. 1. Surgical staple 100 includes a first leg, such as, for example, a backspan 102, and a second leg 104 extending therefrom. Backspan 102 and second leg 104 are substantially coplanar with one another. Backspan 102 has a first linear portion 106 and a second linear portion 108 separated by a protrusion or bump 110. Protrusion or bump 110 has a triangular configuration. Protrusion or bump 110 applies pressure to tissue captured by surgical staple 100. In some embodiments, protrusion or bump 110 may be variously configured, such as, for example, oval, oblong, squared, circular, and/or polygonal.

Second leg 104 has an arcuate configuration and extends between a first end 112 and a second end 114. Second leg 104 may have varying cross section configurations and curvatures between first and second ends 112, 114 to help achieve an optimal shape after deployment. In some embodiments, second leg 104 has a uniform cross section configuration and curvature between first and second ends 112, 114. First end 112 of second leg 104 extends from first linear portion 106 of backspan 102 at an angle such that surgical staple 100 has a generally V-shaped configuration, as shown in FIG. 2. Second end 114 of second leg 104 has a slanted or tapered tip 119 designed and adapted to penetrate tissue. Upon deployment of surgical staple 100, second linear portion 108 of backspan 102 and second end 114 of second leg 104 are brought closer together such that surgical staple 100 takes on a generally D-shaped configuration, as shown in FIG. 3.

Surgical staple 100 can be fabricated from various materials, such as, for example, titanium or stainless steel in the form of sheet metal or wire. In some embodiments, surgical staple 100 or portions thereof are electro-polished to eliminate sharp or rough edges that may otherwise cut, irritate or sever tissue.

With reference to FIGS. 4-8, end effector 120 is provided, and is configured for connection to a distal end of a surgical stapler, such as, for example, surgical fastener applying apparatus 10. End effector 120 includes a cartridge assembly 122 configured to hold or store a plurality of surgical staples, such as, for example, surgical staples 100, and an anvil 124 pivotally attached to cartridge assembly 122 configured to deform surgical staple 100 upon actuation of end effector 120.

Cartridge assembly 122 includes an inner surface 126 defining a cavity or pocket 128 for receipt of surgical staple 100 and a staple guiding member, such as, for example, a staple pusher bar 130. Inner surface 126 includes a first hub 132 and a second hub (not shown) oriented towards one another defining a rotation axis "X1-X1" therebetween. Each hub 132 has a counterbore including a semicircular flat-bottomed hole 134 (FIG. 5) and a smaller hole 136 formed therein configured for rotatable receipt of pusher bar 130.

Inner surface 126 further includes a curved portion 138 configured for receipt of second leg 104 of surgical staple 100 such that second leg 104 is translatable relative to and along curved portion 138 of inner surface 126. A shelf or ledge 140 overlaps curved portion 138 of inner surface 126 to define an opening 142 for second end 114 of second leg 104 to pass through during deployment of surgical staple 100 from cavity 128. Shelf or ledge 140 also provides a stop for pusher bar 130, as described in further detail herein below.

Pusher bar 130 is rotatably disposed in cavity 128. Pusher bar 130 has a first side 150, a second side 152, a top surface 154 and a bottom surface 156 and extends between a first end 158 and a second end 160. First end 158 of pusher bar 130 includes a first disc 162 extending from first side 150 of pusher bar 130 configured for disposal in flat-bottomed hole 134 of hub 132 of cartridge assembly 122. Disc 162 further includes a post 164 extending therefrom having a flattened tip. Post 164 is configured for receipt or disposal in hole 136 of hub 132 of cartridge assembly 122. First end 158 further includes a second disc 172, similar to first disc 162, extending from second side 152 of pusher bar 130 configured for disposal in the flat-bottomed hole of the second hub (not shown) of cartridge assembly 122. Disc 172 further includes a post 174, similar to post 164, having a flattened tip. Post 174 is configured for receipt or disposal in the hole of the second hub (not shown) of cartridge assembly 122.

Posts 164, 174 are oriented in opposite directions relative to one another and provide pusher bar 130 with the ability to rotate within cavity 128 of cartridge assembly 122. It is contemplated that, due to the shape and restrictive features of cavity 128, pusher bar 130 is resisted and/or prevented from rotating in any direction other than counter-clockwise from its starting, vertical orientation within cavity 128, as shown in FIG. 4.

Top surface 154 of pusher bar 130 has a planar portion 176 extending between first and second ends 158, 160 configured for abutment with backspan 102 of surgical staple 100, as shown in FIG. 4. Planar portion 176 includes a bump or protrusion 178 disposed at first end 158 of pusher bar 130 configured for engagement with second linear portion 108 of backspan 102 of surgical staple 100. Pusher bar 130 also includes a stepped surface or raised portion 180 extending from top surface 154 and between first and second ends 158, 160. Surgical staple 100 is received between raised portion 180 and inner surface 126 such that surgical staple 100 is resisted and/or prevented from moving laterally. In this way, when surgical staple 100 is disposed within cavity 128, surgical staple 100 is secured between planar portion 176, raised portion or stepped surface 180, bump or protrusion 178, and inner surface 126 of cartridge assembly 122 to provide guidance for surgical staple 100 during deployment thereof. Pusher bar 130 further includes a shelf or ledge 182 that engages shelf or ledge 140 upon deployment of surgical staple 100 so as to prevent second end 160 of pusher bar 130 from exiting cavity 128.

In assembly, pusher bar 130 is inserted vertically downward into cavity 128 until posts 164, 174 engage first and second hubs 132 in a snap-fit connection. In some embodiments, pusher bar 130 can be inserted from a bottom side of cartridge assembly 122 vertically upward into cavity 128.

Cartridge assembly 122 further includes a driver or sled 184 translatably disposed therein. Driver or sled 184 may include a wedge 186 at a distal end of an arm 188. An upper surface 190 of wedge 186 may taper downwardly to a curved drop off 192. Drop off 192 is configured to engage bottom surface 156 of pusher bar 130 during actuation of end effector 120. In embodiments, cartridge assembly 122 includes a plurality of drivers or sleds 184 configured to engage a plurality of pusher bars 130 in successive order.

Figure 8:
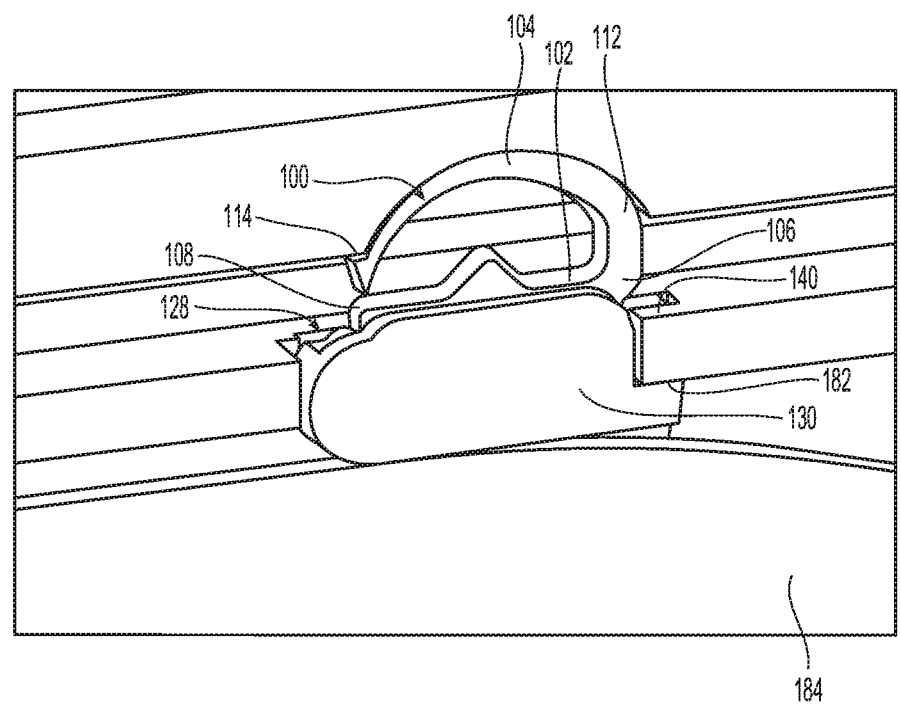
FIG. 8 is a perspective, cutaway view of the end effector shown in FIG. 7 after having formed the surgical staple shown in FIG. 2.

In operation, with tissue disposed between cartridge assembly 122 and anvil 124 of end effector 120, end effector 120 is actuated to pivot cartridge assembly 122 and/or anvil 124 toward the other. Driver or sled 184 translates, in a direction shown by arrow "A" in FIG. 7, and engages wedge 186 with second end 160 of bottom surface 156 of pusher bar 130. Pusher bar 130 rotates about first axis "X1-X1," in a direction shown by arrow "B" in FIG. 7, from the starting, vertical position shown in FIG. 4, to a finished, horizontal position shown in FIG. 8. The rotation of pusher bar 130 causes surgical staple 100 to rotate within cavity 128 relative to and along curved portion 138, such that second leg 104 of surgical staple 100 exits cavity 128 of cartridge assembly 122 and penetrates tissue. Continued rotation of pusher bar 130 and, in turn, rotation of surgical staple 100, engages second leg 104 with an anvil pocket 125 of anvil 124 so as to deform or bend second leg 104 of surgical staple 100 about first linear portion 106 of backspan 102. Deformation of surgical staple 100 ceases upon an engagement of shelf or ledge 182 of pusher bar 130 with shelf or ledge 140 of cartridge assembly 122, as shown in FIG. 8. After surgical staple 100 is formed, surgical staple 100 takes on a generally D-shaped configuration, as shown in FIG. 8, to capture tissue between backspan 102 and second leg 104.

Figure 9:
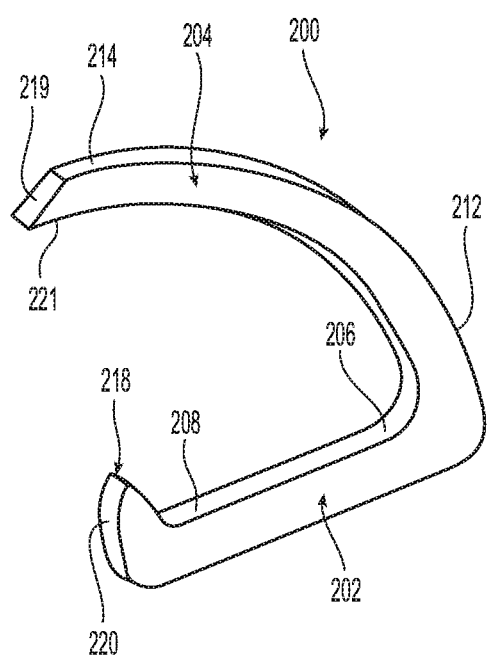
FIG. 9 is a perspective view of a surgical staple in an unformed configuration in accordance with another embodiment of the present disclosure.
Figure 10:
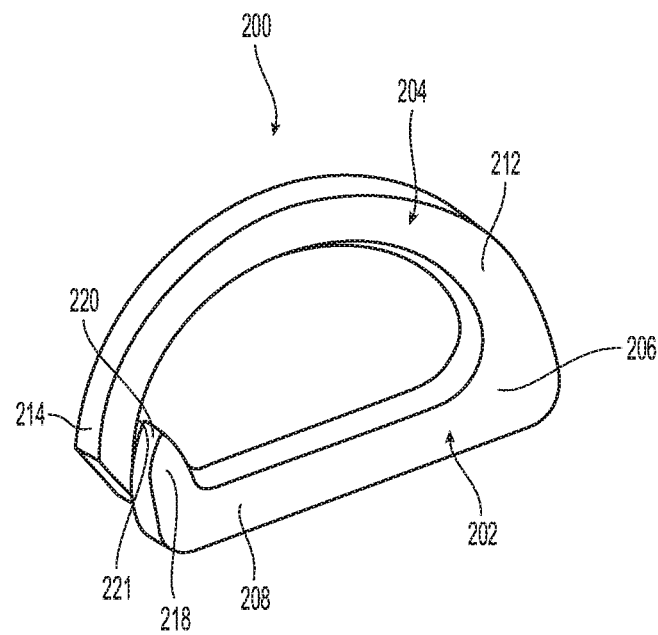
FIG. 10 is a perspective view of the surgical staple shown in FIG. 9 in a formed configuration.

In one embodiment, as shown in FIGS. 9 and 10, a surgical staple 200, similar to surgical staple 100 described above with regard to FIGS. 2-8, is provided. Surgical staple 200, like surgical staple 100, is designed and adapted for use in cartridge assembly 122 of end effector 120 described above. Surgical staple 200 includes a first leg, such as, for example, a backspan 202, and a second leg 204 extending therefrom. Backspan 202 and second leg 204 are coplanar with one another. Backspan 202 has a linear configuration and extends between a first end 206 and a second end 208. Second end 208 of backspan 202 has a bump or short leg 218 extending at an angle therefrom. Bump or short leg 218 helps to stabilize surgical staple 200 in tissue.

Second leg 204 has an arcuate configuration and extends between a first end 212 and a second end 214. Second leg 204 may have a varying cross section configuration and curvature between first and second ends 212, 214 to help achieve an optimal shape after deployment. In some embodiments, second leg 204 may have a uniform cross section and curvature between first and second ends 212, 214. First end 212 of second leg 204 extends from first end 206 of backspan 202 at an angle, such that surgical staple 200 has a generally V-shaped configuration prior to deformation, as shown in FIG. 9. Second end 214 of second leg 204 has a slanted or tapered point 219 designed and adapted to penetrate tissue. Second leg 204 is longer than backspan 202.

In operation, upon deployment of surgical staple 200, second end 208 of backspan 202 and second end 214 of second leg 204 are brought closer together such that surgical staple 200 takes on a generally D-shaped configuration. In the formed configuration, as shown in FIG. 10, a curved inner surface 221 of second end 214 of second leg 204 overlaps and abuts a curved outer surface 220 of short leg 218 of backspan 202 to capture tissue therebetween. In the formed configuration, short leg 218 of backspan 202 and second end 214 of second leg 204 are oriented in opposing directions.

Surgical staple 200 can be fabricated from various materials, such as, for example, titanium or stainless steel in the form of sheet metal or wire. In some embodiments, surgical staple 200 or portions thereof are electro-polished to eliminate sharp or rough edges that may otherwise cut, irritate or sever tissue.

Figure 11:
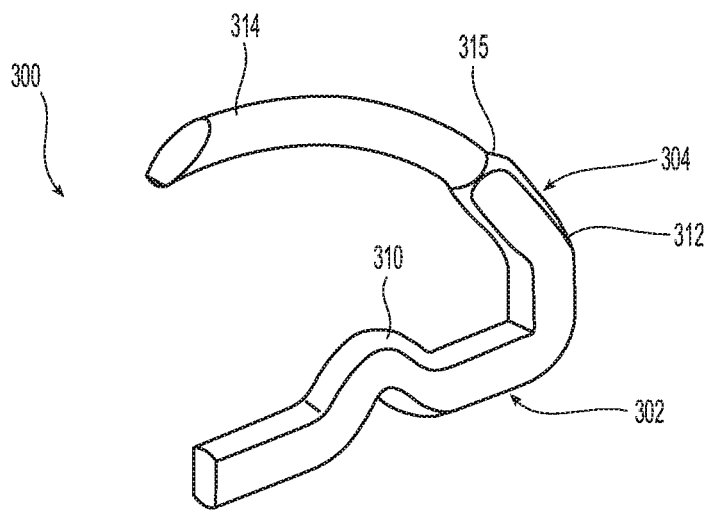
FIG. 11 is a perspective view of a surgical staple in accordance with another embodiment of the present disclosure.

In one embodiment, as shown in FIG. 11, a surgical staple 300, similar to surgical staple 100 described above with regard to FIGS. 2-8, is provided. Surgical staple 300 is fabricated from metallic wire, such as, for example, titanium or stainless steel wire. In embodiments, surgical staple 300 is fabricated from sheet metal. Surgical staple 300 includes a first leg, such as, for example, a backspan 302, and a second leg 304 extending therefrom. Backspan 302 includes a protrusion or bump 310 extending therefrom. Backspan 302 may be flattened, coined, or have an increased thickness to increase a stiffness of backspan 302.

Second leg 304 has a varying cross section and curvature between a first end 312 and a second end 314 to help achieve an optimal shape after deployment. Specifically, first end 312 of second leg 304, similar to backspan 302, may be flattened, coined, or have an increased thickness to increase its stiffness relative to the remainder of second leg 304. Second end 314 of second leg 304 has a uniform rounded cross section configuration such that second end 314 is more pliable and, in turn, more prone to bending or deforming under compressive forces compared to the flattened or coined portions of first and second legs 302, 304. Accordingly, surgical staple 300 may have a higher likelihood of bending at an interface 315 between first and second ends 312, 314 of second leg 304 than along other portions of surgical staple 300.

With reference to FIGS. 12-15, a 3-dimensional surgical staple 400, in accordance with another embodiment of the present disclosure, is provided. Surgical staple 400 is designed and adapted to be deployed directly by a driver or sled 484 without using a pusher bar, as described herein below.

Figure 12:
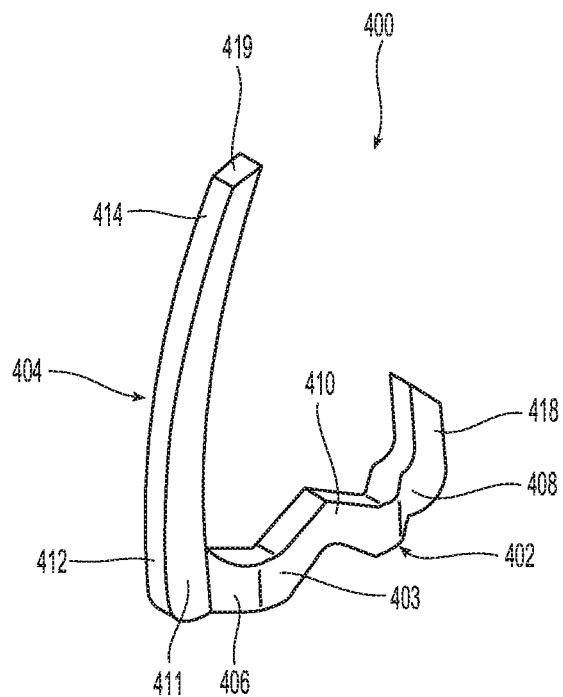
FIG. 12 is a perspective view of a surgical staple in accordance with another embodiment of the present disclosure.
Figure 13:
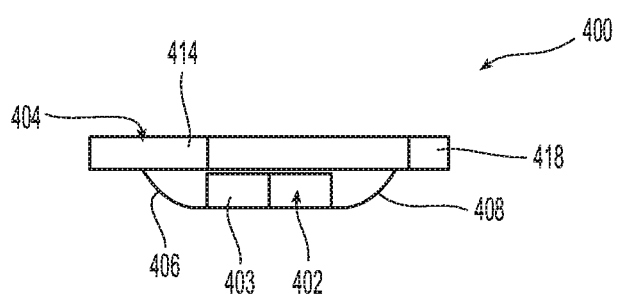
FIG. 13 is a top view of the surgical staple shown in FIG. 12.

Referring specifically to FIGS. 12 and 13, surgical staple 400 includes a first leg, such as, for example, a backspan 402, and a second leg 404 extending therefrom. At least a portion of backspan 402 is non-coplanar with second leg 404 of surgical staple 400. Backspan 402 includes a main body 403 extending between a first end 406 and a second end 408 having a triangular bump or protrusion 410 disposed therebetween. Protrusion or bump 410 provides pressure to tissue captured by surgical staple 400. First end 406 of main body 403 is attached to a side surface 411 of a first end 412 of second leg 404 at an angled orientation relative thereto such that main body 403 of backspan 402 is offset from or disposed in a different plane than second leg 404. Second end 408 of main body 403 of backspan 402 has an extension or short leg 418 extending perpendicularly and upwardly therefrom in parallel alignment with second leg 404. Short leg 418 is offset from main body 403 of backspan 402 and coplanar with second leg 404. Having main body 403 of backspan 402 offset from second leg 404 and short leg 418 allows surgical staple 400 to be translated through a cartridge assembly 422 towards an anvil 424 along backspan 402 while second leg 404 and short leg 418 are guided through cartridge assembly 412, as described in greater detail below.

Second leg 404 has an arcuate configuration and extends upwardly from main body 403 of backspan 402. Second leg 404 may have a varying cross section configuration and curvature between first and second ends 412, 414 to help achieve an optimal shape after deployment. In some embodiments, second leg 404 has a uniform cross section configuration and curvature between first and second ends 412, 414. Second end 414 of second leg 404 has a slanted or tapered tip 419 designed and adapted to penetrate tissue. Upon deployment of surgical staple 400, short leg 418 of backspan 402 and second end 414 of second leg 404 are brought closer together, such that surgical staple 400 may take on a generally D-shaped configuration.

Surgical staple 400 can be fabricated from various materials, such as, for example, titanium or stainless steel in the form of sheet metal or wire. In some embodiments, surgical staple 400 or portions thereof are electro-polished to eliminate sharp or rough edges that may otherwise cut, irritate or sever tissue.

Figure 14:
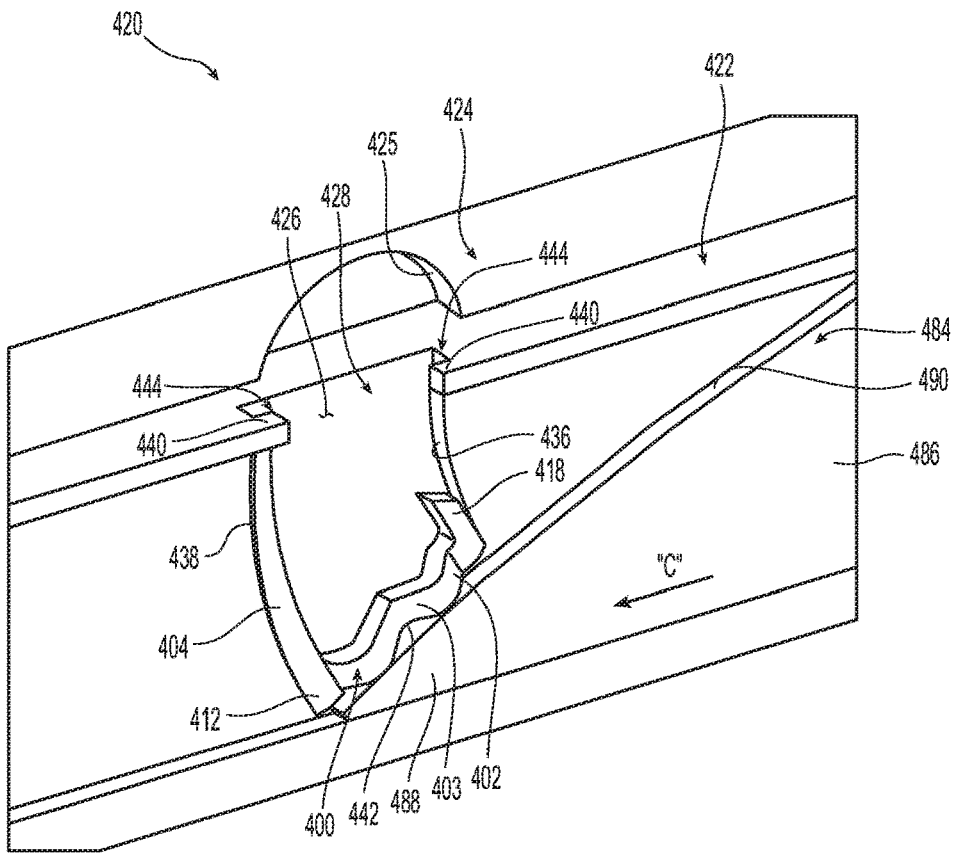
FIG. 14 is a perspective, cutaway view of an end effector, in accordance with an embodiment of the present disclosure, including a cartridge assembly and an anvil having the surgical staple shown in FIG. 12 disposed therein in an unformed position.
Figure 15:
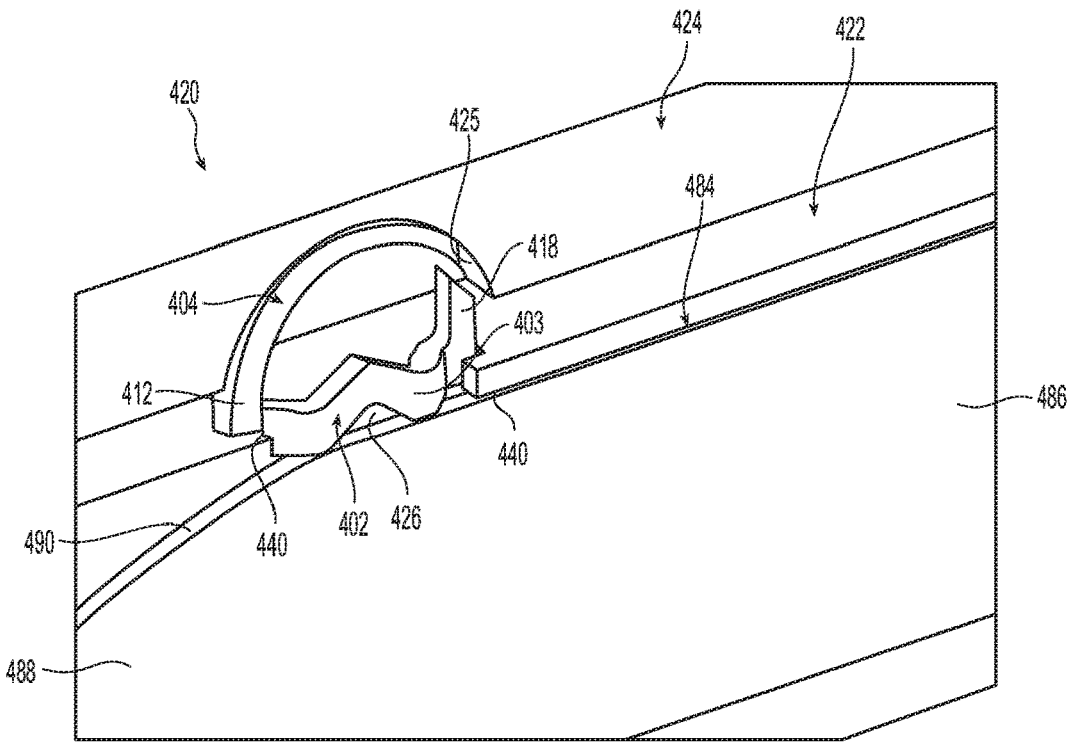
FIG. 15 is a perspective, cutaway view of the cartridge assembly shown in FIG. 14 after having formed the surgical staple shown in FIG. 12.

With reference to FIGS. 14 and 15, an end effector 420 of a surgical stapler is provided. End effector 420 includes a cartridge assembly 422 configured to hold or store a plurality of surgical staples, such as, for example, surgical staples 400, and an anvil 424 configured to deform surgical staple 400 upon actuation of end effector 420.

Cartridge assembly 422 includes an inner surface 426 defining a cavity or pocket 428 configured for receipt of a surgical staple, such as, for example, surgical staple 400. Inner surface 426 includes a curved portion 438 configured for receipt of second leg 404 of surgical staple 400 such that second leg 404 is translatable along and relative to curved portion 438 of inner surface 426. Inner surface 426 further includes a planar portion 442 in juxtaposed relation to curved portion 438 configured for receipt of backspan 402 of surgical staple 400. A pair of oppositely oriented shelves or ledges 440 overlap cavity 428 to define openings 444 configured to capture first end 412 of second leg 404 and short leg 418 of backspan 402 therein during deployment of surgical staple 400 from cavity 428.

Cartridge assembly 422 further includes a driver or sled 484 translatably disposed therein. Driver or sled 484 includes an arm 486 and a wedge 488 at a distal end thereof. An upper surface 490 of wedge 488 is substantially planar and tapers downwardly to a pointed distal tip. Upper surface 490 is configured to engage an underside of main body 403 of backspan 402 during actuation of end effector 420. In embodiments, cartridge assembly 422 includes a plurality of drivers or sleds 484 configured to engage a plurality of surgical staples 400 in successive order.

In operation, with tissue disposed between cartridge assembly 422 and anvil 424 of end effector 420, end effector 420 is actuated to pivot or translate cartridge assembly 422 and/or anvil 424 toward the other. Driver or sled 484 is translated, in a direction shown by arrow "C" in FIG. 14, into engagement with an underside of backspan 402 of surgical staple 400. As driver or sled 484 is further translated, an upwardly oriented force is acted on surgical staple 400 as a result of the tapered configuration of upper surface 490 of wedge 488. Surgical staple 400 is guided through cavity 428 by inner surface 426 and shelves or ledges 440. Continued translation of driver or sled 484 and, in turn, movement of surgical staple 400 through cavity 428 of cartridge assembly 422, engages second leg 404 with an anvil pocket 425 of anvil 424 so as to deform or bend second leg 404 about first end 406 of backspan 402. Deformation of surgical staple 400 ceases upon the abutment of upper surface 490 of arm 486 of driver or sled 484 with shelves or ledges 440 of cartridge assembly 422, as shown in FIG. 15. In a deployed position, as shown in FIG. 15, backspan 402 of surgical staple 400 is in parallel alignment with shelves or ledges 440 of cartridge assembly 422. After surgical staple 400 is formed, surgical staple 400 takes on a generally D-shaped configuration to capture tissue between backspan 402 and second leg 404.

Figure 16:
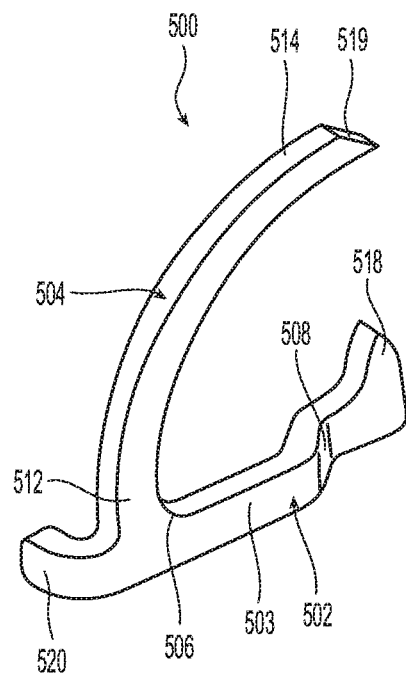
FIG. 16 is a perspective view of a surgical staple in an unformed configuration in accordance with another embodiment of the present disclosure.
Figure 17:
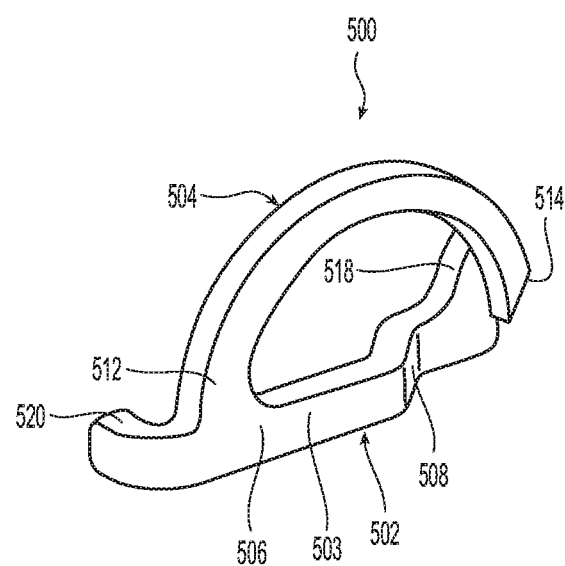
FIG. 17 is a perspective view of the surgical staple shown in FIG. 16 in a formed configuration.
Figure 21:
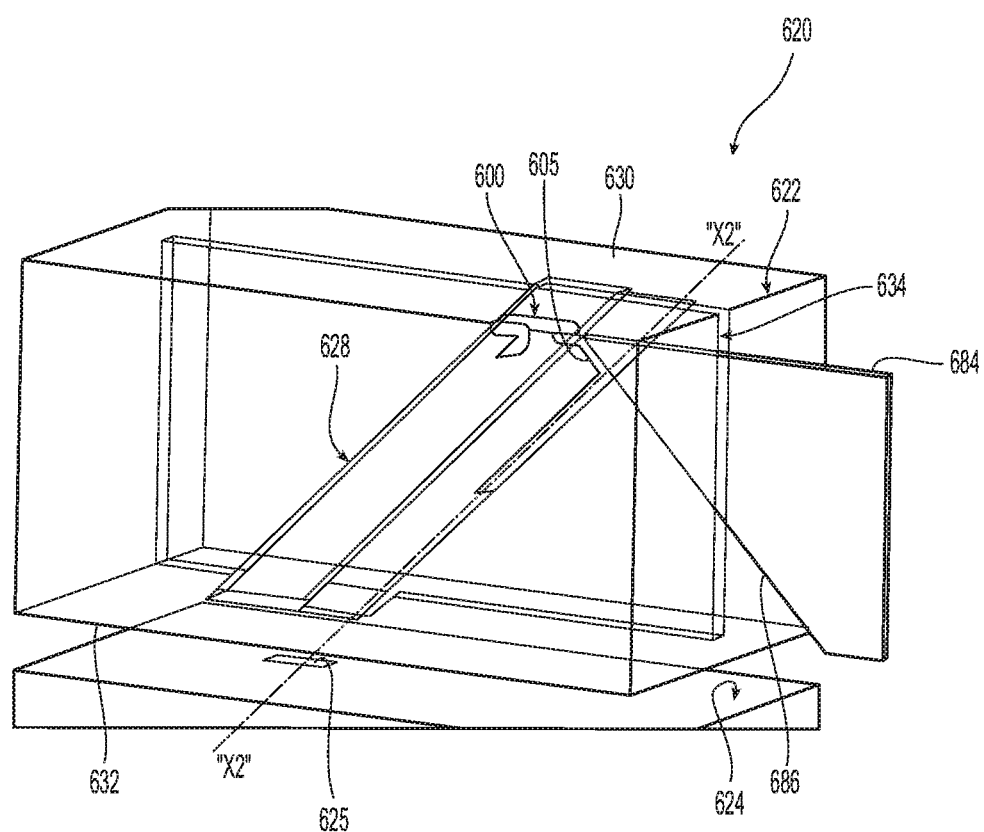
FIG. 21 is a perspective view of a cartridge assembly and anvil of an end effector, in accordance with an embodiment of the present disclosure, having the surgical staple shown in FIG. 18A disposed therein.

With reference to FIGS. 16 and 17, another embodiment of a 3-dimensional surgical staple designated as 500 is provided, similar to surgical staple 400 described above with regard to FIGS. 12-15. Surgical staple 500 is designed and adapted to be deployed directly by a driver or sled without using a pusher bar, similar to surgical staple 400 described above. Surgical staple 500 includes a first leg, such as, for example, a backspan 502, and a second leg 504 extending therefrom. At least a portion of backspan 502 is non-coplanar with second leg 504. Backspan 502 includes a main body 503 extending between a first end 506 and a second end 508. First end 506 of main body 503 is attached to a first end 512 of second leg 504. Backspan 502 includes an extension or short leg 518 extending upwardly from second end 508 of main body 503. Short leg 518 is offset from main body 503 of backspan 502.

Second leg 504 of surgical staple 500 has an arcuate configuration and extends between a first end 512 and a second end 514. Second leg 504 may have a varying cross section configuration and curvature between first and second ends 512, 514 to help achieve an optimal shape after deployment. In some embodiments, second leg 504 has a uniform cross section configuration and curvature between first and second ends 512, 514. First end 512 of second leg 504 extends from first end 506 of main body 403 of backspan 502 at an angle such that surgical staple 500 has a generally V-shaped configuration, as shown in FIG. 16. Second end 514 of second leg 504 has a slanted or tapered tip 519 designed and adapted to penetrate tissue. Upon deployment of surgical staple 500, short leg 518 of backspan 502 and second end 514 of second leg 504 are brought closer together such that surgical staple 500 takes on a generally D-shaped configuration, as shown in FIG. 17. In the formed configuration, second end 514 of second leg 504 is in a side-by-side orientation with short leg 518 of backspan 502 to capture tissue therebetween.

Surgical staple 500 further includes a lateral extension or hook 520 connected to at least one of first end 506 of backspan 502 and first end 512 of second leg 504. Hook 520 is configured for translatable receipt in a track formed in a cartridge assembly. At least a portion of hook 520 and short leg 518 are co-planar with one another.

Surgical staple 500 can be fabricated from various materials, such as, for example, titanium or stainless steel in the form of sheet metal or wire. In some embodiments, surgical staple 500 or portions thereof are electro-polished to eliminate sharp or rough edges that may otherwise cut, irritate or sever tissue.

With reference to FIGS. 18A-24, a self-supporting, self-locking surgical staple 600, in accordance with another embodiment of the present disclosure, is provided. Surgical staple 600 is designed and adapted to be self-supporting within its respective pocket or channel 628 of a cartridge assembly 622, as described in further detail below. Surgical staple 600 is also designed and adapted to self-lock or have its legs interlock upon deployment to provide more reliable tissue compression and hemostasis of said tissue.

Surgical staple 600 includes a first leg, such as, for example, a backspan 602, and a second leg 604. Backspan 602 has a plurality of bends along its length forming a plurality of segments along its length. A first segment 603 is connected to and extends perpendicularly from a first end 612 of second leg 604. First segment 603 interconnects backspan 602 with second leg 604. A second segment 605 extends upwardly at an angle, for example, substantially 90 degrees, relative to first segment 603. The angle at which second segment 605 extends from first segment 603 is relatively small to minimize any loss of driving force of surgical staple 600 through cartridge assembly 622 due to friction and to minimize the need to increase a thickness of an interface between first and second segments 603, 605 to prevent deformation at the interface. Second segment 605 is configured for abutting engagement with a driver or wedge 684 to translate surgical staple 600 through cartridge assembly 622 and into tissue. Second segment 605 interconnects first segment 603 with a third segment 607 of surgical staple 600.

Third segment 607 is connected to second segment 605 at an obtuse angle. Backspan 602 includes a squared or hooked portion 609 connected to third segment 607. Squared or hooked portion 609 defines a notch 611 configured for disposal of a second end 614 of second leg 604. Squared or hooked portion 609 is designed and adapted to retain or lock second end 614 of second leg 604 in notch 611 in a formed configuration of surgical staple 600. Backspan 602 further includes an extension or short leg 618 extending transversely and downwardly therefrom, such that short leg 618 runs parallel with second leg 604, as shown in FIG. 19A. Short leg 618 further has a pointed tip 619 configured for penetrating tissue.

Second leg 604 has a linear configuration and a circular, uniform cross section configuration. In some embodiments, second leg 604 is variously configured and has various cross section configurations, such as, for example, those alternatives described herein above. Second leg 604 extends between a first end 612 and a second end 614. As mentioned above, first end 612 is connected to first segment 603 of backspan 602. Second end 614 has a pointed end 616 configured for penetrating tissue.

In use, surgical staple 600 is shaped or bent to change surgical staple 600 from a starting, unformed configuration, as shown in FIGS. 18A, 19A, and 20A, to a finished, formed configuration, as shown in FIGS. 18B, 19B, and 20B. To change surgical staple 600 from the unformed configuration to the formed configuration, surgical staple 600 is brought into engagement with an anvil 624 that directs a compressive force upon second leg 604 of surgical staple 600. Second end 614 of second leg 604 is bent or curved relative to first end 612 of second leg 604 until second end 614 of second leg 604 is received within notch 611 of backspan 602 and in abutment with squared or hooked portion 609 of backspan 602, such that backspan 602 and second leg 604 are interlocked with one another. In the formed configuration, as shown in FIGS. 18B, 19B and 20B, second end 614 of second leg 604 and short leg 618 of backspan 602 are oriented in opposing directions to better capture tissue therebetween.

With reference to FIGS. 21-24, an end effector 620 of a surgical stapler is provided. End effector 620 includes a cartridge assembly 622 configured to hold or store a plurality of surgical staples, such as, for example, surgical staples 600, and an anvil 624 pivotally or translatably attached to cartridge assembly 622 and configured to deform surgical staple 600 upon actuation of end effector 620.

Cartridge assembly 622 includes a pocket or channel 628 adapted and designed for receipt of a surgical staple, such as, for example, surgical staple 600. Pocket or channel 628 is shaped and dimensioned to closely surround surgical staple 600 so as to resist and/or prevent movement of surgical staple 600 in all directions except along an axis "X2-X2." In this way, surgical staple 600 is supported within pocket or channel 628, as shown in FIG. 23, without a need for any additional restrictive components, such as, for example, a pusher bar 130. Pocket or channel 628 extends transversely between a top end 630 and a bottom surface 632 of cartridge assembly 622. For example, pocket or channel 628 can extend at an acute angle relative to both top end 630 and bottom surface 632 of cartridge assembly 622.

Cartridge assembly 622 further includes a driver or wedge 684. Driver or wedge 684 has a planar driving surface 686. Driver or wedge 684 is translatably disposed in an elongate channel 634 defined in cartridge assembly 622. Elongate channel 634 overlaps pocket or channel 628. Driving surface 686 of driver or wedge 684 abuts second segment 605 of surgical staple 600 and is disposed at an angle with respect to second leg 604 of surgical staple 600. In embodiments, cartridge assembly 622 includes a plurality of drivers or wedges 684 configured to engage a plurality of surgical staples 600 in successive order.

In operation, with tissue disposed between cartridge assembly 622 and anvil 624 of end effector 620, end effector 620 is actuated to pivot or translate cartridge assembly 622 and/or anvil 624 toward the other. Driver or wedge 684 is translated, in a direction shown by arrow "D" in FIG. 22, into engagement with second segment 605 of backspan 602 of surgical staple 600. As driver or wedge 684 is further translated, a force is acted on surgical staple 600, in a direction along axis "X2-X2," to translate surgical staple 600 through pocket or channel 628. Continued translation of driver or wedge 684 and, in turn, movement of surgical staple 600 through pocket or channel 628 of cartridge assembly 622, engages second leg 604 with an anvil pocket 625 of anvil 624 so as to deform or bend second end 614 of second leg 604 about first end 612 of second leg 604. After surgical staple 600 is formed, second end 614 of second leg 604 interlocks with squared or hooked portion 609 of backspan 602, as shown in FIGS. 18B, 19B, and 20B, to capture tissue between backspan 602 and second leg 604.

In one embodiment, as shown in FIGS. 25A and 25B, a surgical staple 700 is provided, similar to surgical staple 600 described above with regard to FIGS. 18A-24. Surgical staple 700, like surgical staple 600, is designed and adapted to be self-supporting within its respective pocket or channel of a cartridge assembly. Surgical staple 700 is also designed and adapted to self-lock or have its legs interlock upon deployment to provide more reliable tissue compression and hemostasis of said tissue.

Surgical staple 700 includes a first leg, such as, for example, a backspan 702, and a second leg 704. Backspan 702 has a plurality of bends along its length forming a plurality of segments along its length such that at least a portion of backspan 702 is offset from second leg 704. A first segment 703 is connected to and extends perpendicularly from a first end 712 of second leg 704. First segment 703 interconnects backspan 702 with second leg 704. A second segment 705 extends upwardly at an angle relative to first segment 703. Second segment 705 is configured for abutting engagement with a driver or wedge to translate surgical staple 700 through a cartridge assembly and into tissue. Second segment 705 interconnects first segment 703 with a third segment 707 of surgical staple 700.

Third segment 707 is connected to second segment 705 at an obtuse angle. Backspan 702 includes a squared or hooked portion 709 connected to third segment 707 to help retain surgical staple 700 in a pocket or channel of a cartridge assembly, such as, for example, a pocket or channel similar to that founding cartridge assembly 622. Backspan 702 further includes an extension or short leg 718 extending transversely and downwardly therefrom, such that short leg 718 runs parallel with second leg 704, as shown in FIG. 25A. Short leg 718 has a pointed tip 719 configured for penetrating tissue.

Second leg 704 has a linear configuration and a circular, uniform cross section configuration. Second leg 704 extends between a first end 712 and a second end 714. As mentioned above, first end 712 is connected to first segment 703 of backspan 702. Second end 714 has a pointed end 716 configured for penetrating tissue.

In use, surgical staple 700 is shaped or bent to change surgical staple 700 from a starting, unformed configuration, as shown in FIG. 25A, to a finished, formed configuration, as shown in FIG. 25B. To change surgical staple 700 from the unformed configuration to the formed configuration, surgical staple 700 is brought into engagement with an anvil that directs a compressive force upon second leg 704 of surgical staple 700. Second end 714 of second leg 704 is bent or curved relative to first end 712 of second leg 704 until second end 714 of second leg 704 is in juxtaposed relation to and abutment with short leg 718 of backspan 702. In this way, backspan 702 and second leg 704 are interlocked with one another. In the formed configuration, as shown in FIG. 25B, second end 714 of second leg 704 and short leg 718 of backspan 702 are oriented in opposing directions to better capture tissue therebetween.

In one embodiment, as shown in FIGS. 26A-27, a surgical staple 800 is provided, similar to surgical staple 700 described above with regard to FIGS. 25A and 25B. Surgical staple 800, like surgical staple 700, is designed and adapted to be self-supporting within its respective pocket or channel of a cartridge assembly. Surgical staple 800 is also designed and adapted to self-lock or have its legs interlock upon deployment to provide more reliable tissue compression and hemostasis of said tissue.

Surgical staple 800 includes a first leg, such as, for example, a backspan 802, and a second leg 804. Backspan 802 has a plurality of bends along its length forming a plurality of segments along its length such that at least a portion of backspan 802 is offset from second leg 804. A first segment 803 is connected to and extends perpendicularly from a first end 812 of second leg 804. First segment 803 interconnects backspan 802 with second leg 804. A second segment 805 extends upwardly at an angle relative to first segment 803. Second segment 805 is configured for abutting engagement with a driver or wedge to translate surgical staple 800 through a cartridge assembly and into tissue. Second segment 805 interconnects first segment 803 with a third segment 807 of surgical staple 800.

Third segment 807 is connected to second segment 805 at an obtuse angle. Backspan 802 includes a squared or hooked portion 809 connected to third segment 807 to help retain surgical staple 800 in a pocket or channel of a cartridge assembly, such as, for example, a pocket or channel similar to that found in cartridge assembly 622 described above. Backspan 802 further includes an extension or short leg 818 extending transversely and downwardly therefrom, such that short leg 818 runs substantially parallel with second leg 804, as shown in FIG. 26A. Short leg 818 has a length that is approximately half of a length of second leg 804. In some embodiments, short leg 818 has a length that is more or less than a length of second leg 804. Short leg 818 has an arcuate configuration and a uniform cross section configuration. In some embodiments, short leg 818 is variously shaped and configured, such as, for example, those alternatives described herein above. Short leg 818 also has a pointed tip 819 configured for penetrating tissue.

Second leg 804 has a linear configuration and a circular, uniform cross section configuration. Second leg 804 extends between a first end 812 and a second end 814. As mentioned above, first end 812 is connected to first segment 803 of backspan 802. Second end 814 has a pointed end 816 configured for penetrating tissue.

With reference to FIG. 27, an anvil 824 is provided to apply a compressive force on surgical staple 800. Anvil 824 includes two anvil pockets 825, 827 oriented perpendicular relative to one another so that both second leg 804 and short leg 818 can be deformed about two axes that lie in perpendicular relation to one another. Anvil pocket 825 is configured for engagement with second leg 804 and anvil pocket 827 is configured for engagement with short leg 818. Anvil pocket 825 is longer than anvil pocket 827 because second leg 804 is to be bent or curved to a substantially lesser degree than short leg 818.

In use, surgical staple 800 is shaped or bent to change surgical staple 800 from a starting, unformed configuration, as shown in FIG. 26A, to a finished, formed configuration, as shown in FIG. 26B. To change surgical staple 800 from the unformed configuration to the formed configuration, surgical staple 800 is brought into engagement with anvil 824 that directs a compressive force upon both second leg 804 and short leg 818 of backspan 802.

Second end 814 of second leg 804 is bent or curved relative to first end 812 of second leg 804 about a first axis "X3-X3" until second end 814 of second leg 804 is substantially parallel with third segment 807 and squared or hook portion 809 of backspan 802. First end 812 of second leg 814 may be fabricated from a more pliable material or have a lesser thickness than the remainder of second leg 804 so that bending of second leg 804 occurs adjacent first end 812, as shown in FIG. 26B. After second end 614 of second leg 604 is bent or curved to a position juxtaposed to short leg 818, short leg 818 contacts anvil pocket 827 of anvil 824 causing short leg 818 to bend or curve about an axis "X4-X4," substantially perpendicular to axis "X3-X3," about which second leg 804 is bent or curved. Short leg 818 is bent or curved around second end 814 of second leg 804 to interlock backspan 802 and second leg 804 with one another. In the formed configuration, as shown in FIG. 26B, short leg 818 takes on a U-shaped configuration.

It is contemplated that each of the surgical staples described herein may be fabricated from different materials at certain preselected areas of the surgical staples and/or may have different thicknesses or densities at certain preselected areas thereof to ensure bending or curving of the surgical staples at said preselected areas of the surgical staples. Further, it is envisioned that the various segments or components of the surgical staples disclosed herein may be monolithically formed or integrally connected with one another. It is further contemplated that the various end effectors and surgical staples described herein can be integrated with a variety of surgical staplers other than the surgical stapler shown in FIG. 1, such as, for example, a surgical stapler-cutter, a linear surgical stapler, a linear surgical stapler-cutter, a circular surgical stapler, or a circular surgical stapler-cutter.

Although specific embodiments of the present disclosure have been described above in detail, it will be understood that this description is merely for purposes of illustration. Various modifications of and equivalent structures corresponding to the disclosed aspects of the embodiments in addition to those described above may be made by those skilled in the art without departing from the spirit of the present disclosure which is defined in the following claims, the scope of which is to be accorded the broadest interpretation so as to encompass such modifications and equivalent structures.

What is claimed is:

1. An end effector for a surgical stapler, the end effector comprising:
   an anvil including a staple forming surface that defines therein:
      a first staple forming pocket configured to engage an end of a long leg of a staple; and
      a second staple forming pocket disposed adjacent the first staple forming pocket, the second staple forming pocket being configured to engage an end of a short leg of the staple; and
   a cartridge assembly movably coupled to the anvil between unapproximated and approximated positions, the cartridge assembly defining a longitudinal axis and a pocket extending at an angle relative to the longitudinal axis, the pocket of the cartridge assembly supporting the staple therein, the cartridge assembly including a driver configured to move the staple into engagement with the staple forming surface of the anvil to deform the staple, wherein the first anvil pocket is longer than the second anvil pocket, such that the first anvil pocket deforms the long leg to a lesser degree than the second anvil pocket deforms the short leg.

2. The end effector according to claim 1, wherein the first and second staple forming pockets are perpendicular to one another.

3. The end effector according to claim 2, wherein each of the first and second staple forming pockets has an elongated configuration.

4. The end effector according to claim 3, wherein the first staple forming pocket defines a first longitudinal axis, and the second staple forming pocket defines a second longitudinal axis that is perpendicular to the first longitudinal axis of the first staple forming pocket.

5. The end effector according to claim 1, wherein the end of the short leg of the staple is configured to curve around the end of the long leg of the staple upon deformation of the staple.

6. The end effector according to claim 1, wherein the first anvil pocket is parallel with a longitudinal axis defined by the anvil, and the second anvil pocket is perpendicular to the longitudinal axis defined by the anvil.

7. The end effector according to claim 1, wherein the first anvil pocket is configured to deform the long leg about a first axis, and the second anvil pocket is configured to deform the short leg about a second axis that is perpendicular to the first axis.

8. The end effector according to claim 1, wherein the pocket of the cartridge assembly is configured to direct movement of the staple along an axis defined by the pocket of the cartridge assembly, the axis of the pocket of the cartridge assembly extending at an acute angle relative to the longitudinal axis of the cartridge assembly.

9. The end effector according to claim 1, wherein the driver has a planar driving surface, the driver being translatable along the longitudinal axis of the cartridge assembly such that engagement of the planar driving surface of the driver with the staple urges the staple towards engagement with the staple forming surface of the anvil to deform the staple.

10. The end effector according to claim 9, wherein the cartridge assembly defines an elongate channel for housing the driver, the elongate channel intersecting the pocket of the cartridge assembly.

11. An anvil configured to apply a compressive force on a surgical staple, the surgical staple having a long leg and a short leg, the anvil comprising:
   a staple forming surface defining therein:
      a first staple forming pocket configured to engage an end of the long leg of the staple; and
      a second staple forming pocket disposed adjacent the first staple forming pocket, the second staple forming pocket being configured to engage an end of the short leg of the staple, wherein the first anvil pocket is configured to deform the long leg about a first axis, and the second anvil pocket is configured to deform the short leg about a second axis that is perpendicular to the first axis.

12. The anvil according to claim 11, wherein the first and second staple forming pockets are perpendicular to one another.

13. The anvil according to claim 12, wherein each of the first and second staple forming pockets has an elongated configuration.

14. The anvil according to claim 13, wherein the first staple forming pocket defines a first longitudinal axis, and the second staple forming pocket defines a second longitudinal axis that is perpendicular to the first longitudinal axis of the first staple forming pocket.

15. The anvil according to claim 11, wherein the first anvil pocket is longer than the second anvil pocket, such that the first anvil pocket deforms the long leg to a lesser degree than the second anvil pocket deforms the short leg.

16. The anvil according to claim 11, wherein the first anvil pocket is parallel with a longitudinal axis defined by the anvil, and the second anvil pocket is perpendicular to the longitudinal axis defined by the anvil.

17. An anvil configured to apply a compressive force on a surgical staple, the surgical staple having a long leg and a short leg, the anvil comprising:
   a staple forming surface defining therein:
      a first staple forming pocket configured to engage an end of the long leg of the staple; and
      a second staple forming pocket disposed adjacent the first staple forming pocket, the second staple forming pocket being configured to engage an end of the short leg of the staple, wherein the first anvil pocket is configured to deform the long leg about a first axis, and the second anvil pocket is configured to deform the short leg about a second axis that is non-parallel to the first axis.

18. The anvil according to claim 17, wherein the first staple forming pocket defines a first longitudinal axis, and the second staple forming pocket defines a second longitudinal axis that is perpendicular to the first longitudinal axis of the first staple forming pocket.

19. The anvil according to claim 17, wherein the first anvil pocket is longer than the second anvil pocket, such that the first anvil pocket deforms the long leg to a lesser degree than the second anvil pocket deforms the short leg.

20. The anvil according to claim 17, wherein the first anvil pocket is parallel with a longitudinal axis defined by the anvil, and the second anvil pocket is perpendicular to the longitudinal axis defined by the anvil.

* * * * *